US005697954A

United States Patent [19]
Sears et al.

[11] Patent Number: 5,697,954
[45] Date of Patent: Dec. 16, 1997

[54] DEFIBRILLATION SYSTEM INCLUDING AN ATRIAL DEFIBRILLATOR AND VENTRICULAR DEFIBRILLATION BACKUP

[75] Inventors: Gena K. Sears, Seattle, Wash.; Jerry C. Griffin, Chicago, Ill.

[73] Assignee: InControl, Inc., Redmond, Wash.

[21] Appl. No.: 641,783

[22] Filed: May 2, 1996

[51] Int. Cl.$^6$ .................................................. A61N 1/39
[52] U.S. Cl. .................................................. 607/5
[58] Field of Search .................................. 607/5, 6, 7, 8

[56] References Cited

U.S. PATENT DOCUMENTS 5,314,430  5/1994  Bardy ............................................. 607/5
5,372,605  12/1994  Adams et al. .................................. 607/5

Primary Examiner—Scott M. Getzow
Attorney, Agent, or Firm—Richard O. Gray, Jr.

[57] ABSTRACT

An implantable defibrillation system includes a lead system for making electrical contact with a heart, an atrial cardiovertor coupled to the lead system for applying cardioverting electrical energy to that is of the heart, and a ventricular defibrillator coupled to the lead system. The ventricular defibrillator includes a ventricular arrhythmia detector responsive to a control signal for detecting for a ventricular arrhythmia of the heart and a ventricular cardiovertor for cardioverting the ventricles of the heart in response to the ventricular arrhythmia detector detecting a ventricular arrhythmia. A ventricular arrhythmia detector enable stage provides the control signal in response to each application of cardioverting electrical energy to the atria by the atrial cardiovertor.

10 Claims, 1 Drawing Sheet

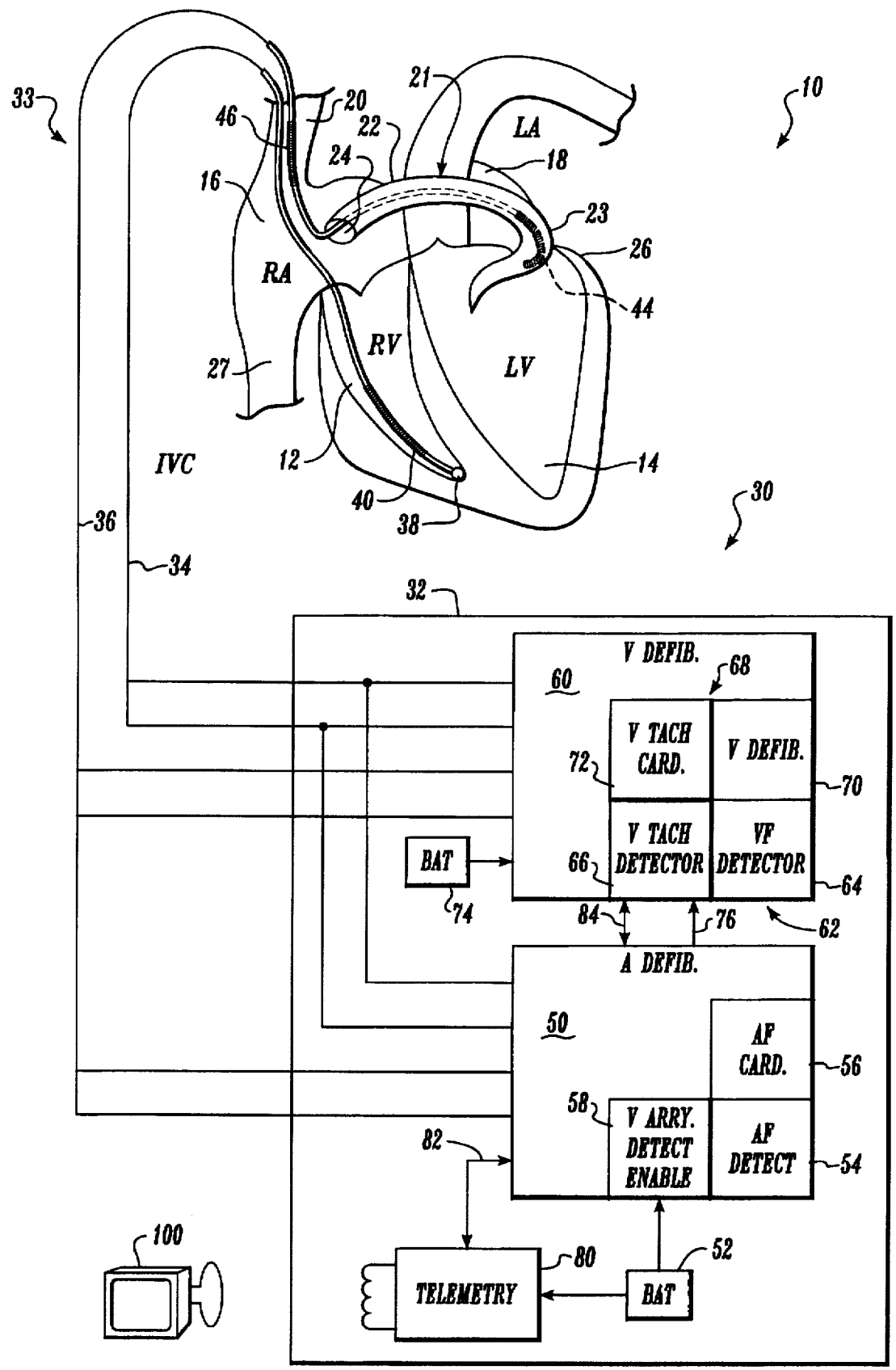

DEFIBRILLATION SYSTEM INCLUDING AN ATRIAL DEFIBRILLATOR AND VENTRICULAR DEFIBRILLATION BACKUP

BACKGROUND OF THE INVENTION

The present invention generally relates to an atrial defibrillator for applying cardioverting electrical energy to the atria of a human heart in need of cardioversion. The present invention is more particularly directed to an implantable defibrillation system including a fully automatic atrial defibrillator and a ventricular defibrillator which is enabled for ventricular fibrillation or tachycardia detection and cardioversion after each delivery of cardioverting electrical energy to the atria by the atrial defibrillator.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well know in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, when successful, it most often only results in temporary relief for patients, lasting but a few weeks.

Drugs are available for reducing the incidence of atrial fibrillation. However, these drugs have many side effects and many patients are resistant to them or are unable to tolerate them which greatly reduces their therapeutic effect.

Implantable atrial defibrillators have been proposed to provide patients suffering from occurrences of atrial fibrillation with relief. Two such proposed defibrillators, although represented as being implantable, were not fully automatic, requiring human interaction for cardioverting or defibrillating the heart. Both of these proposed defibrillators require the patient to recognize the symptoms of atrial fibrillation, with one defibrillator requiring a visit to a physician to activate the defibrillator, and the other defibrillator requiring the patient to activate the defibrillator with an external magnet. However, both of these defibrillators did provide synchronizing the delivery of the defibrillating or cardioverting electrical energy to the atria with a ventricular electrical activation (R wave) of the heart. This is important for reducing the risk of inducing a ventricular arrhythmia such as ventricular fibrillation. Ventricular fibrillation is a fatal arrhythmia which can be caused by electrical energy being delivered to the heart at the wrong time in the cardiac cycle, such as during the T wave of the cycle.

Another measure for essentially eliminating the risk of inducing ventricular fibrillation as a result of the delivery of cardioverting electrical energy to the atria of the heart is described in U.S. Pat. No. 5,207,219, which issued on May 4, 1993, for ATRIAL DEFIBRILLATOR AND METHOD FOR PROVIDING INTERVAL TIMING PRIOR TO CARDIOVERSION, and which patent is also assigned to the assignee of the present invention. As described in that patent, it has been observed that during episodes of atrial fibrillation, the cardiac rate may increase to a high rate. At high cardiac rates, the R wave of each cardiac cycle becomes closely spaced from the T wave of the immediately preceding cardiac cycle. This may lead to a condition known in the art as an "R on T" condition which is believed to contribute to induced ventricular fibrillation if the atria are cardioverted in synchronism with an R wave close to a T wave.

The atrial defibrillator and method described in U.S. Pat. No. 5,207,219 greatly reduces this risk by avoiding applying the cardioverting electrical energy to the atria at those instances when increased vulnerability to ventricular fibrillation may be present. This is accomplished by interval timing prior to applying the cardioverting or defibrillating electrical energy. The time interval between immediately successive R waves is timed and the cardioverting or defibrillating electrical energy is applied when a timed interval is greater than a preselected minimum interval. This provides protection for the increased vulnerability to ventricular fibrillation condition resulting from a high cardiac rate.

It has been further observed in U.S. Pat. No. 5,486,198 which issued on Jan. 23, 1996, for ATRIAL DEFIBRILLATOR AND METHOD FOR PROVIDING INTERVAL TIMING OF SUCCESSIVE INTERVALS PRIOR TO CARDIOVERSION, and which is also assigned to the assignee of the present invention, that during atrial fibrillation the cardiac rate can be highly variable with a long cardiac cycle being followed by a relatively short cardiac cycle. This condition in conjunction with a high cardiac rate may cause a dispersion of refractoriness and also may result in an increased vulnerability to ventricular fibrillation or tachycardia during atrial cardioversion. Suggests a further condition be applied to the timed interval, requiring the timed interval to also be less than a preselected maximum interval before the cardioverting or defibrillating energy is applied to the atria. Hence, while the minimum interval criteria has proven essential in providing safe cardioversion of the atria, it is observed in U.S. Pat. No. 5,486,198 that a minimum interval sufficiently long so as to be safe under all conditions limits the number of cardiac cycles which would satisfy the minimum interval criteria. This correspondingly limits the probability of locating an R wave with which to synchronize the cardioverting energy delivery.

The aforementioned U.S. Pat. No. 5,486,198 describes how the number of such available cycles for synchronizing the energy delivery may be increased while still maintaining safety. This is accomplished by requiring a predefined relationship or criteria to be satisfied between a current cardiac interval (one to be used for synchronization) and the interval immediately preceding the current interval. If that criteria is satisfied, the energy may still be delivered safely even though the current interval is less than a minimum interval considered safe under all conditions.

The present invention represents an alternative approach for insuring patient safety during atrial cardioversion. In general, the present invention provides a defibrillation system wherein the intended therapy is atrial defibrillation but which also includes a ventricular defibrillator. The ventricular defibrillator includes a ventricular fibrillation detector which detects for ventricular fibrillation in response to and immediately after each attempted cardioversion of the atria. If ventricular fibrillation is detected, the ventricular defibrillator cardioverts the ventricles.

SUMMARY OF THE INVENTION

The present invention provides an implantable defibrillation system including a lead system having at least one lead which in turn has at least one electrode for making electrical contact with a heart. The system further includes an atrial cardiovertor coupled to the lead system for applying cardioverting electrical energy to the atria of the heart and a ventricular defibrillator coupled to the lead system. The ventricular defibrillator includes a ventricular arrhythmia detector which is responsive to a control signal for detecting for a ventricular arrhythmia of the heart and a ventricular cardiovertor for cardioverting the ventricles of the heart in response to the ventricular arrhythmia detector detecting a ventricular arrhythmia. The system further includes ventricular arrhythmia detector enable means for providing the control signal in response to each application of cardioverting electrical energy to the atria by the atrial cardiovertor.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the sole FIGURE of which like reference numerals identify identical elements, and wherein the sole FIGURE is a schematic block diagram of a fully implantable defibrillation system embodying the present invention for providing atrial cardioversion of the illustrated human heart as a primary therapy and ventricular defibrillation/cardioversion as a backup therapy should a ventricular arrhythmia be induced as a result of applying defibrillating or cardioverting electrical energy to the atria of the heart.

DETAILED DESCRIPTION OF THE PREFERRED EMBODIMENT

Referring now to the sole FIGURE, it illustrates a fully implantable defibrillation system 30 embodying the present invention shown in association with a schematically illustrated human heart 10 in need of atrial fibrillation monitoring and potential cardioversion of the atria. The portions of the heart 10 illustrated in the FIGURE are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27. In addition, as used herein, the term "electrical activations" denotes R waves of the heart cardiac cycle which are depolarizations of the ventricles 12 and 14.

The defibrillation system 30 generally includes an enclosure 32 for hermetically sealing the internal circuit elements of the defibrillation system to be described hereinafter, and a system lead 33. The enclosure 32 and lead system 33 are arranged to be implanted beneath the skin of a patient so as to render the defibrillation system 30 fully implantable.

The lead system 33 includes an endocardial first lead 34. The lead 34 has a distal sensing electrode 38 and a proximal elongated defibrillation electrode 40 arranged for establishing electrical contact with the right ventricle 12 of the heart 10. The electrodes 38 and 40 permit bi-polar sensing of ventricular activations in the right ventricle and electrode 40 provides for ventricular cardioversion/defibrillation as will be described subsequently. As illustrated, the lead 34 is preferably fed through the superior vena cava 20, into the right atrium 16, and then into the right ventricle 12 as illustrated with electrode 38 being at the apex of the right ventricle 12.

The lead system also includes a second lead 36 which includes a first electrode 44 and a second, proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first electrode 44 is within the coronary sinus channel 21, either within the coronary sinus 22 adjacent the left ventricle 14 and beneath the left atrium 18, or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16.

The lead system 33 is very versatile. The first electrode 44 together with the second electrode 46 provide bi-polar sensing of heart activity in the atria 16 and 18. The first electrode 44 and the second electrode 46 are elongated to further provide for the delivery of defibrillating electrical energy to the atria. Also, the ventricles may be defibrillated by connecting electrodes 44 and 46 in common and applying defibrillating electrical energy between electrode 40 and the combined electrodes 44 and 46. Alternatively, the ventricles may be defibrillated by applying defibrillating electrical energy either between electrodes 40 and 44 or electrodes 40 and 46. Electrodes 40 and 38 provide bi-polar sensing of ventricular activity. Lastly, electrodes 40 and 38 may be used for delivering tachycardia treatment to the ventricles as by overdrive pacing, for example.

Within the enclosure 32, the defibrillation system 30 generally includes an atrial cardiovertor/defibrillator 50 and a ventricular cardiovertor/defibrillator 60. Aside from sharing the lead system 33, the cardiovertors 50 and 60 are each stand alone, fully functional devices.

The atrial defibrillator 50 is powered by its own battery 52. The defibrillator 50 includes an atrial fibrillation detector 54, an atrial fibrillation cardiovertor 56, and a ventricular arrhythmia detector enable stage 58.

The ventricular defibrillator/cardiovertor 60 includes a ventricular arrhythmia detector 62 including a ventricular fibrillation detector 64 and a ventricular tachycardia detector 66. Such detectors are well known in the art. The ventricular defibrillator/cardiovertor 60 further includes a ventricular defibrillator/cardiovertor stage 68 including a ventricular defibrillation stage 70 and a ventricular cardiovertor 72, each of a type well known in the art. Like the atrial defibrillator 50, the ventricular defibrillator/cardiovertor 60 is powered by its own battery 74. As will be seen hereinafter the battery 74 preferably has less stored energy than battery 52 to conserve on space within the enclosure 32.

Lastly, the enclosure 32 contains telemetry 80. Telemetry 80 permits the defibrillators 50 and 60 to communicate with an external programmer 100 of the type known in the art. The telemetry is preferably powered by the battery 52. To support the communication between programmer 100 and the defibrillators 50 and 60, telemetry 80 is coupled to the atrial defibrillator 50 by a bi-directional bus 82 and to the ventricular defibrillator 60 through defibrillator 50 and by another bi-directional bus 84.

In operation, the atrial fibrillation detector 54 may be implemented as described in U.S. Pat. No. 5,464,432, issued Nov. 7, 1995 and incorporated herein by reference. To that end, the atrial fibrillation detector may be activated at spaced apart times to detect for atrial fibrillation of the atria 16 and 18 of the heart 10. Atrial activity, sensed between electrodes 44 and 46 is used for this determination. If the detector 54 fails to detect atrial fibrillation, therapy is not administered and the detector 54 is deactivated until next activation time is reached. However, if the detector 54 does detect the presence of atrial fibrillation, the detector 54 then activates the atrial fibrillation cardiovertor 56.

The cardiovertor 56 includes a storage capacitor (not shown) as is well known in the art. It is charged to a voltage believed to be sufficient for defibrillating the atria 16 and 18 to return the atria to normal sinus rhythm. Once the capacitor is fully charged, the cardiovertor 56 discharges the capacitor and applies the cardioverting voltage to electrodes 44 and 46 of lead 36. The capacitor is preferably discharged in synchronism with an R wave detected across electrodes 38 and 40.

Immediately after the capacitor discharge of cardiovertor 56, the ventricular arrhythmia enable 58 generates a control signal which is delivered to the ventricular defibrillator 60 over a control line 76. The control signal causes the ventricular arrhythmia detector 62 to detect for a ventricular arrhythmia which may have been induced by the attempted cardioversion of the atria by cardiovertor 56. Preferably, the ventricular arrhythmia detector 62 is responsive to only the control signal for detecting a possible ventricular arrhythmia. Since ventricular fibrillation is immediately life threatening, the ventricular fibrillation detector 64 first detects for ventricular fibrillation by analyzing ventricular activity sensed between electrodes 38 and 40. If ventricular fibrillation is not present, then ventricular tachycardia detector detects for possible ventricular tachycardia, again by analyzing ventricular activity sensed between electrodes 38 and 40.

If neither ventricular fibrillation nor ventricular tachycardia is detected, the atrial fibrillation detector 54 will then determine if the cardioversion attempt was successful. If it was successful, the system 30 is deactivated until the next activation time of detector 54. If it was not successful, however, the cardiovertor 56 is again activated to once again apply cardioverting voltage to the atria, and preferably at a higher voltage than used in the last attempt. Of course, immediately after the repeated cardioversion attempt, the control signal is once again generated.

If the detector 64 detects ventricular fibrillation, the ventricular defibrillation stage is activated to apply vigorous defibrillation therapy to the ventricles 12 and 14. This may be accomplished by the stage 70 connecting electrodes 44 and 46 together and applying energy on the order of 15 to 40 joules, for example, between the connected electrode pair 44 and 46 and electrode 40. This provides two simultaneous shock vectors to cover both ventricular myocardium masses, one from electrode 38 to electrode 46 and the other from electrode 38 to electrode 44. After this is completed, the detectors 64 and 66 preferably perform a redetection.

In providing the discharge of 15–40 joules of energy, the defibrillation stage 70 may include its own separate energy storage capacitors. However, to conserve on space, the defibrillation stage 70 and atrial cardiovertor 56 may share capacitors with the cardiovertor 50 making use of all or only a portion of the total number of capacitors for cardioverting the atria.

If the detector 64 initially fails to detect ventricular fibrillation but the detector 66 detects ventricular tachycardia, the cardiovertor 72 is activated to apply antitachycardia therapy to the ventricles. This may be accomplished by the ventricular tachycardia cardiovertor providing overdrive pacing pulses to electrodes 38 and 40 in a manner known to the art.

Whether it is ventricular fibrillation or ventricular tachycardia which is detected and treated, such treatment should be continued until the arrhythmia is terminated. Once terminated, the atrial fibrillation detector 54 may then perform another detection followed by the appropriate action, either deactivation or continued atrial therapy.

As previously mentioned, the battery 74 has less initial stored energy than battery 52. This is to conserve on space within enclosure 32 and is consistent with the degree of use to be expected of battery 74. To illustrate, the atrial defibrillator 50 may have an expected lifetime of three to four years. Over this lifetime, its detector 54 may be activated at thirty minute intervals and its cardiovertor 56 may be called upon to deliver 1000 shocks to the atria at an energy of, for example, one to five joules. For this expected use, battery 52 may initially have stored about two and a half (2.5) amp-hours of energy at a battery voltage two and a half (2.5) volts.

A finite probability of an atrial cardioversion shock inducing a ventricular arrhythmia has been observed in the art. That probability, while not being determined to date for all atrial fibrillation patients taken as a whole and with no other safety measure but synchronization, appears to be between approximately one-tenth to one percent. Hence, out of 1000 atrial cardioversion shocks, worst case, one might expect ten (10) ventricular arrhythmia episodes to be induced. Assuming that all ten (10) are ventricular fibrillation requiring the most energy to terminate, the initial energy storage of battery 74 need only be on the order of 0.2 to 0.5 amp-hours at 2.5 volts. This assumes an average ventricular defibrillating shock of 30 joules, a charging efficiency of sixty percent (60%), a battery voltage of 2.5 volts, and typical required power to support detection and other overhead. Hence, the initial energy capacity of battery 74 need only be a fraction of the initial energy capacity of battery 52.

Hence, the present invention provides an alternative approach in providing safe atrial fibrillation therapy. After each attempted cardioverison of the atria, a control signal is generated to cause a ventricular arrhythmia detector to detect for a ventricular arrhythmia such as defibrillation. Vigorous ventricular therapy may then be used to terminate the ventricular arrhythmia.

While a particular embodiment of the invention has been shown and described, modification can be made, and it is therefore intended to cover in the appended claims all such changes and modifications which fall within the true spirit and scope of the invention.

What is claimed is:

1. An implantable defibrillation system comprising:
   a lead system including at least one lead having at least one electrode for making electrical contact with a heart;
   an atrial cardiovertor coupled to the lead system for applying cardioverting electrical energy to the atria of the heart;
   a ventricular defibrillator coupled to the lead system including a ventricular arrhythmia detector responsive to a control signal for detecting for a ventricular arrhythmia of the heart and a ventricular cardiovertor for cardioverting the ventricles of the heart in response to the ventricular arrhythmia detector detecting a ventricular arrhythmia; and
   ventricular arrhythmia detector enable means for providing the control signal in response to each application of cardioverting electrical energy to the atria by the atrial cardiovertor.

2. A system as defined in claim 1 wherein the ventricular cardiovertor includes a ventricular tachycardia cardiovertor and wherein the ventricular arrhythmia detector includes a ventricular tachycardia detector.

3. A system as defined in claim 1 wherein the ventricular cardiovertor includes a ventricular fibrillation cardiovertor and wherein the ventricular arrhythmia detector includes a ventricular fibrillation detector.

4. A system as defined in claim 1 wherein the ventricular arrhythmia detector includes a ventricular fibrillation detector and a ventricular tachycardia detector.

5. A system as defined in claim 4 wherein the ventricular fibrillation detector detects for ventricular fibrillation before the ventricular tachycardia detector detects for ventricular tachycardia.

6. A system as defined in claim 1 further including a first battery to power the atrial cardiovertor and a second battery to power the ventricular defibrillator.

7. A system as defined in claim 6 wherein the first battery has an initial energy capacity, wherein the second battery has an initial energy capacity, and wherein the initial energy capacity of the first battery is greater than the initial energy capacity of the second battery.

8. A system as defined in claim 6 wherein the first battery stores an initial quantity of energy, wherein the quantity of energy initially stored in the first battery is sufficient to sustain X number of atrial fibrillation cardioversions, wherein the quantity of energy initially stored in the second battery is sufficient to sustain Y number of ventricular fibrillation cardioversions, and wherein Y is a fraction of X.

9. A system as defined in claim 1 wherein the ventricular arrhythmia detector is responsive to only the control signal for detecting for a ventricular arrhythmia of the heart.

10. An implantable defibrillation system comprising:

a lead system including at least one lead having at least one electrode for making electrical contact with a heart;

an atrial defibrillator coupled to the lead system for applying cardioverting electrical energy to the atria of the heart; and a ventricular defibrillator coupled to the lead system including a ventricular fibrillation detector for detecting for ventricular fibrillation of the heart and a ventricular cardiovertor for cardioverting the ventricles of the heart in response to the ventricular fibrillation detector detecting ventricular fibrillation, said ventricular fibrillation detector being responsive to each application of cardioverting electrical energy to the atria by the atrial cardiovertor for detecting for ventricular fibrillation.

* * * * *